United States Patent [19]

Huber et al.

[11] Patent Number: 5,198,537
[45] Date of Patent: Mar. 30, 1993

[54] DIGOXIGENIN DERIVATIVES AND USE THEREOF

[75] Inventors: Erasmus Huber, Garching; Klaus Mühlegger, Polling; Herbert von der Eltz, Weilheim; Bruno Zink, Staffelsee, all of Fed. Rep. of Germany

[73] Assignee: Boehringer Mannheim GmbH, Mannheim, Fed. Rep. of Germany

[21] Appl. No.: 427,249

[22] Filed: Oct. 25, 1989

[30] Foreign Application Priority Data

Oct. 27, 1988 [DE] Fed. Rep. of Germany ....... 3836656

[51] Int. Cl.$^5$ ..................... C07H 21/04; C07D 41/00; C07D 19/00; G01N 33/53
[52] U.S. Cl. .................................. 530/406; 536/6.1; 536/26.26; 540/104; 540/105
[58] Field of Search ................ 540/104, 105; 424/1.1; 536/28, 6.1, 27; 530/406, 345, 405, 388.24

[56] References Cited

U.S. PATENT DOCUMENTS

| | | | |
|---|---|---|---|
| 3,855,208 | 12/1974 | Ruthol et al. | 540/104 |
| 3,925,355 | 12/1975 | Plasia et al. | 424/1.1 |
| 4,064,227 | 12/1977 | Brown et al. | 424/1.1 |
| 4,082,747 | 4/1978 | Chen | 540/105 |
| 4,469,797 | 9/1984 | Albarella | 436/536 |

FOREIGN PATENT DOCUMENTS

| | | |
|---|---|---|
| 0173251 | 3/1986 | European Pat. Off. . |
| 0174753 | 3/1986 | European Pat. Off. . |
| 604164 | 8/1978 | Switzerland ........... 540/105 |
| 2003480 | 12/1978 | United Kingdom . |

OTHER PUBLICATIONS

Olivier et al., J. Clin. Invest. 47:1035–1042 (1968).
Barbieri et al., Clin. Chim. Acta 77: 257–267 (1977).
Castro et al., Meth. Enzymol. 73: 523–543 (1977).
Hinds et al., Clin. Chem. 32(1): 16–21 (1986).
Laebke et al., "Immunologische Teste für niedermolekulare Worstoffe" 1–53 & 117–120.
Monji et al., Experentia 36: 1141–1143 (1980).
Forster et al., Nucl. Acids Res. 13(3): 745–761 (1985).
Wilchek et al., Anal. Biochem. 171: 1–32 (1988).
Monji, et al., Experientia 36(10): 1141–1143 (1980).

Primary Examiner—Robert T. Bond
Assistant Examiner—E. C. Ward
Attorney, Agent, or Firm—Felfe & Lynch

[57] ABSTRACT

The present invention provides digoxigenin derivatives of the formula:

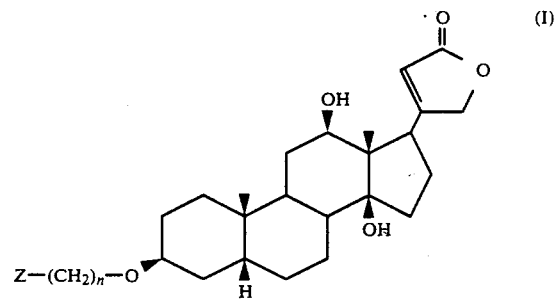

wherein n is a whole number of from 1 to 4 and Z is a carboxyl group or a functional derivative derived therefrom. The present invention also provides digoxigenin conjugates of the general formula:

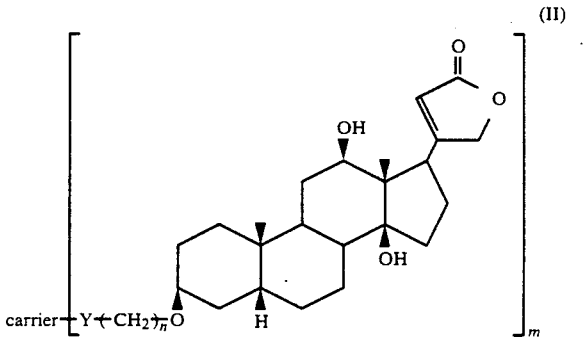

wherein the carrier is an immunogenic carrier material, a nucleic acid or a labelled immunocomponent of a labelled digoxigenin immunoconjugate for use in an immunoassay, m is a number from 1 to the number of coupling positions available on the carrier and Y is the group formed by the reaction of the carboxyl function Z of the digoxigenin derivative of general formula (I) with the reacting position of the carrier material. Also described are uses of these conjugates as nucleic acid probes, immunogens, and in immunoassay.

6 Claims, No Drawings

DIGOXIGENIN DERIVATIVES AND USE THEREOF

The present invention is concerned with new digoxigenin derivatives and processes for the preparation thereof, as well as with the use thereof.

Digoxigenin derivatives in which the basic structure of the digoxigenin is present bound covalently to another molecule or to a macromolecular carrier are used for a large number of bioanalytical purposes. In particular, such digoxigenin derivatives are used in immunological tests (immunoassays) for determinations of cardiotonic glycosides, especially digoxin, which are important from the therapeutic point of view (cf. G. C. Oliver et al., J. Clin. Invest., 47, 1035/1968; U. Barbieri and C. Gandolfi, Clin. Chim. Acta, 77, 257/1977; A. Castro and N. Monji, "Immunochemical Methods", Part B, published by J. L. Langone and H. van Vunakis, Academic Press, 1981, p. 523; J. A. Hinds et al., Clinical Chemistry, 32, 16/1986). In these tests, the digoxigenin derivatives are used in combination with antibodies against the cardiotonic glycosides to be determined and the detection takes place via the hapten anti-hapten antibody exchange reaction principle (cf. K. Luebke and B. Nieuweboer, "Immunologische Tests fur niedermolekulare Wirkstoffe", Thieme Verlag, Stuttgart, 1978).

As digoxigenin derivatives, those derivatives in which the digoxigenin is bound covalently via the 3-position of the steroid structure to the other molecule are generally used.

However, such digoxigenin derivatives display one or more of the following disadvantages:

In the case of a linkage via an ester group with the digoxigenin steroid structure, the digoxigenin derivatives are very base labile because of the sensitivity to hydrolysis of the ester grouping under basic conditions. This is particularly true for the hemisuccinates and hemiglutarates usually employed (cf. Swiss Patent Specification No. 604,164 which corresponds to U.S. patent application Ser. No. 782,160, filed Mar. 28, 1977 and apparently abandoned; U.S. Pat. No. 4,082,747; N. Monji et al., Experientia, 36, 1141/1980). This also applies, for example, to the urethane grouping used instead of the ester grouping (cf. U.S. Pat. No. 4,064,227). Therefore under certain conditions an undesired splitting off of the digoxigenin can result.

Apart from the 3-position of the steroid structure, digoxigenin also has a reactive hydroxyl group at the 12-position; in the case of the preparation of the derivatives, a mixture of 3- and 12-derivatives is often obtained which, in some cases, can only be separated into pure positional isomers via considerable preparative expenditure and in some cases, for example in the case of the preferably used hemisuccinates and hemiglutarates, they cannot be separated chromatographically. However, the use of non-separated mixtures can lead to erroneous results.

In the derivatives, the steroid structure can, in part, be modified in such a manner that recognition of the hapten by an antibody directed against the unmodified steroid basic structure can be strongly impaired. This is the case, for example, with digoxigenin derivatives in which the oxygen atom in the 3-position is replaced by amino nitrogen (cf., for example, U.S. Pat. No. 4,469,797).

Therefore, it is an object of the present invention to provide digoxigenin derivatives which are well suited for immunological tests for the determination of cardiotonic glycosides and with which the above-described disadvantages can be avoided.

Thus, according to the present invention, there are provided digoxigenin derivatives of the general formula:

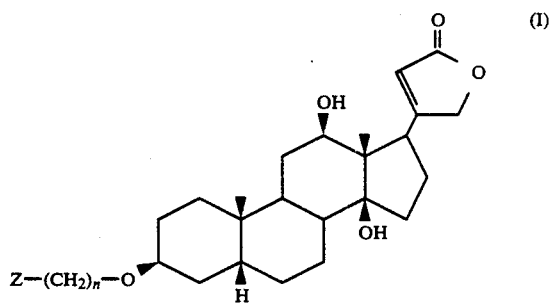

wherein n is a whole number of from 1 to 4 and is preferably 1 and Z is a carboxyl group or a functional derivative derived therefrom.

Z is preferably the group —COOH, —CN, —COOR$^5$, —CONR$^1$R$^2$, —COONR$^3$R$^4$, —CON COOCOR$_5$, or wherein R$^1$, R$^2$, R$^3$ and R$^4$, independently of one another, are hydrogen atoms or alkyl, aralkyl or aryl radicals or R$^1$ and R$^2$ or R$^3$ and R$^4$ together can also form a carbocyclic or heterocyclic ring system and R$^5$ or R$^6$ is an alkyl or aralkyl radical, preferably containing from 1 to 7 carbon atoms, especially methyl, ethyl, propyl, isobutyl, phenyl or benzyl. Especially preferred alkyls for R$^5$ and R$^6$ are ethyl, isobutyl or benzyl.

In the above-mentioned radicals, the alkyl radicals can be branched. Preferably, they are straight-chained. The alkyl radical preferably contains up to 12 and especially 2 to 8 carbon atoms. An alkyl radical can also be interrupted by one or more heteroatoms, for example oxygen, or can be unsubstituted or substituted by, e.g., an amino group, which itself may be subsituted.

The aryl radical can be a mono- or polynuclear carbo- or heterocyclic aromatic radical, preferably with 6 to 14 ring atoms. It can be unsubstituted or substituted. Preferred is phenyl. The aralkyl radical has 7-14 ring atoms and is derived from the above-defined alkyl and aryl radicals and can be, for example, a benzyl or phenethyl radical.

The group —CONR$^1$R$^2$ can be, for example, the —CONH—(CH$_2$CH$_2$O)$_2$—CH$_2$CH$_2$NH$_2$ radical in which the NH$_2$ group can be substituted, preferably by a 4-azidobenzoyl radical. The —COONR$^3$R$^4$ group is preferably an N-hydroxysuccinimide ester grouping:

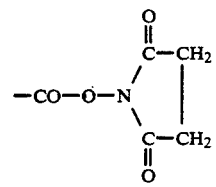

or one of the following groupings:

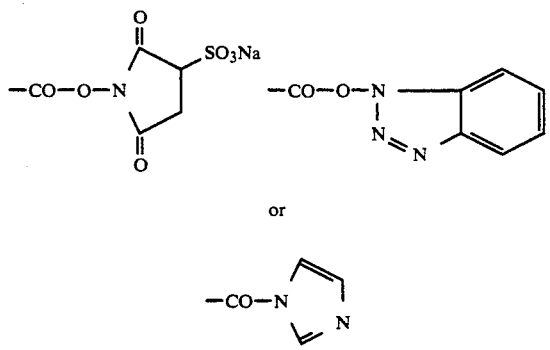

In the digoxigenin derivatives of general formula (I) according to the present invention, the binding between the steroid structure and the bridge takes place via an ether bond in the 3-position, the base lability involved with an ester grouping thereby being avoided. Furthermore, the functional, i.e., oxy group present in the digoxigenin steroid structure in the 3-position is thereby maintained. This results in better recognition of the hapten by the antibody, which, as a rule, is directed against the non-modified steroid structure. The ether bond in the 3-position in accordance with this invention also makes possible the preparation of the compounds of general formula (I) and the derivatives and conjugates thereof as pure positional isomers, i.e. with the avoidance of a mixture of derivatives which are bound in the 3- and 12-position.

The preparation of the compounds of general formula (I) according to the present invention can take place starting from 12-O-acetyldigoxigenin (in the following reaction scheme, compound 3), which is obtainable in known manner from digoxin (compound 1) after conversion into the pentaacetyldigoxin (compound 2) and acidic saponification. In the 12-O-acetyldigoxigenin, the free hydroxyl group in the 3-position is now converted into the ether grouping $Z—(CH_2)_2—O—$. This reaction can take place with a diazocarboxylic acid ester, for $n=1$ for example with a diazoacetic acid ester, in known manner with the formation of the 3-alkoxycarbonylalkyl ether ($Z=COOR^5$; corresponds to compound 4). If desired, in the alkoxycarbonylalkyl ester obtained, the ester group can be converted by saponification into the free carboxyl group ($Z=COOH$; compound 5) or into another functional carboxylic acid grouping Z and, if desired, in a reaction product obtained in this way, the group Z can be converted in known manner into another group Z. By reaction with N-hydroxysuccinimide, the COOH group can be converted, for example, into the grouping $—COONR^3R^4$ ($R^3$ and $R^4$ together form the 1,4-dioxotetramethylene radical; compound 6). This grouping can be converted by reaction with an amine $NHR^1R^2$ into the compound (I) with $Z=CONR^1R^2$ (corresponds to compound 7). In this or similar known way, it is possible to convert a compound obtained of general formula (I), in which Z has one of the above-given meanings, into another compound of general formula (I) with a different meaning for Z.

The individual above-mentioned process steps, for example the reaction with a diazoacetic acid ester, the saponification steps, the reaction with N-hydroxysuccinimide and the reaction with an amine $NHR^1R^2$, can take place in the usual way for these reactions, for example as is explained in the following examples.

A further important field of use for the digoxigenin derivatives is also the use thereof for labelling and detecting nucleic acids and nucleic acid derivatives. In German Patent Applications P 38 00 644.8 (12th Jan., 1988) and P 38 13 278.8 (20th Apr., 1988) is described a process for the detection of nucleic acids by hybridization with a complementary nucleic acid probe which contains at least one hapten as label bound via chemical compounds. As hapten, a steroid is used which does not participate in hydrogen bridge formation on at least one position of the probe and which is bound to the probe via a bridge of at least 4 atoms length. The hybridized probe is detected via a labelled anti-hapten antibody. As steroid, digoxigenin or digoxin is preferred. If the hapten is incorporated into the nucleic acid probe photochemically with the help of a photohapten (cf. Nucl. Acid Res., 13, 745–761/1985; and M. Wilchek and E. S. Bayer, Anal. Biochem. 171, 1/1988), then as photohapten, photodigoxigenin is preferably used, i.e. a digoxigenin bound via a bridge and having a 4-azidobenzoyl radical. In the case of ultra-violet irradiation, which causes splitting of nitrogen from the azido group, a nitrene radical results which then binds covalently to the nucleic acid. As photodigoxigenin, there is used digoxigenin-3-hemisuccinate [N'-(4-azidobenzoyl)]-8-amino-3,6-dioxaoctylamide.

On the basis of their properties and especially on the basis of the base stability and their unmodified steroid structure, the digoxigenin derivatives of the present invention are very well suited as label haptens for the above-mentioned processes. As photohapten a digoxigenin of general formula (I) is used wherein one of the radicals $R^1$, $R^2$, $R^3$, $R^4$ and/or $R^5$ carries a 4-azidobenzoyl radical, for example N-[N-(4-azidobenzoyl)-8-amino-3,6-dioxaoctyl]-3-carbamoylmethyldigoxigenin (compound 7 of the reaction scheme).

With the digoxigenin derivatives of the present invention, it is possible to bind the oxygen at the 3-position of the steroid without modification of the basic structure, via a bridge molecule to an immunogenic carrier material, such as a protein or polypeptide carrier material, or to a nucleic acid.

The digoxigenin derivatives of general formula (I) according to the present invention are very well suited for the preparation of labelled conjugates such as are used for the determination of cardiotonic glycosides and especially of digoxin, in conventional immunoassays. Appropriate conjugates can, for example, be radio-actively labelled in accordance with standard methods or can be labelled with a fluorescence grouping. The labelled structural unit or moiety is, in the preferred homogeneous techniques, for example an enzyme substrate, a prosthetic group, and enzyme modulator or an enzyme which is coupled with the inventive digoxigenin derivative to give the conjugate.

The binding to the carrier material, to the nucleic acid or to the labelled structural unit takes place via the grouping $—O—(CH_2)_n—Z$, in which Z is preferably chosen depending upon the carrier material and the groups or bonds thereof which react with Z. The linking of the carrier material with the $—O—(CH_2)_n—Z$ group preferably takes place via primary or secondary amino groups which are reacted with an activated carboxylic acid function Z, for example with H-hydroxysuccinimide ester ($Z=—COONR^3R^4$; $R^3$ and $R^4$ together form a 1,4-dioxotetramethylene radical), the reaction thereby taking place in a manner known for such reactions. However, the group —O—$(CH_2)_n$—Z can also be bound to the carrier, for example a nucleic acid, by photochemical methods (cf. Nucl. Acid Res., 13, 745-761/1985; and M. Wilchek and E. A. Bayer, Anal. Biochem., 171, 1/1988). In this case, the carrier material, for example a nucleic acid probe, is irradiated with visible light containing a proportion of ultra-violet light in the presence of the above-mentioned photo-digoxigenin (see reaction scheme, compound 7), in which case, with the splitting off of nitrogen, a nitrene radical results which binds covalently to the nucleic acid.

Therefore, a subject of the present invention is also the use of digoxigenin derivatives of general formula (I) for the preparation of labelled conjugates for the determination of cardiotonic glycosides, especially of digoxin, in conventional immunoassays and the use thereof as labelled hapten for the detection of nucleic acids by hybridization with a complementary nucleic acid probe which, via a chemical bond, contains at least one hapten as label.

A further subject of the present invention are also the new digoxigenin conjugates having the general formula:

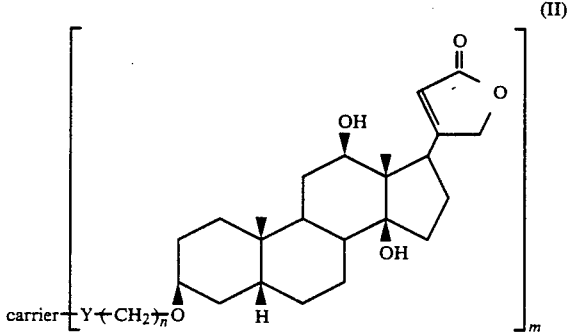

wherein the carrier is an immunogenic carrier material, for example an immunogenic protein or polypeptide carrier material, a nucleic acid or a labelling moiety of a labelled digoxigenin conjugate for use in immunoassays, m is a number of from 1 up to the number of the coupling positions available on the carrier and is preferably from 1 to 20 and Y is the group formed by the reaction of the carboxyl function Z of the digoxigenin derivatives of general formula (I) according to the present invention with the reacting position of the carrier material, for example an amide group.

A further subject of the present invention is the use of the digoxigenin conjugates of general formula (II), wherein the carrier is an immunogen, for the immunization of organisms suitable for antibody formation. In using a conjugate as described supra wherein the carrier is an immunogen, antibodies can be produced which can then be used in one of the conventional immunoassay processes for the determination of digoxin. Examples of such processes include agglutination techniques, radio-immunoassays, heterogeneous enzyme immunoassays, heterogeneous fluorescence immunoassays and homogeneous immunoassays. The preparation and isolation of these antibodies, including monoclonal antibodies, takes place in known manner.

A further subject of the present invention is the use of the digoxigenin conjugates of general formula (II), in which the carrier represents the labelled structural unit of a labelled digoxigenin conjugate, in conventional immunoassays for the determination of cardiotionic glycosides, especially of digoxin.

The following examples are given for the purpose of illustrating the present invention. If not states otherwise, the statements of amount are parts by weight and ambient temperature is to be understood to be a temperature of 25°±2° C.

EXAMPLES

The following reaction scheme A gives a survey of the syntheses illustrated in the examples of the digoxigenin derivatives of general formula (I) according to the present invention and the method of carrying them out:

Reaction scheme A

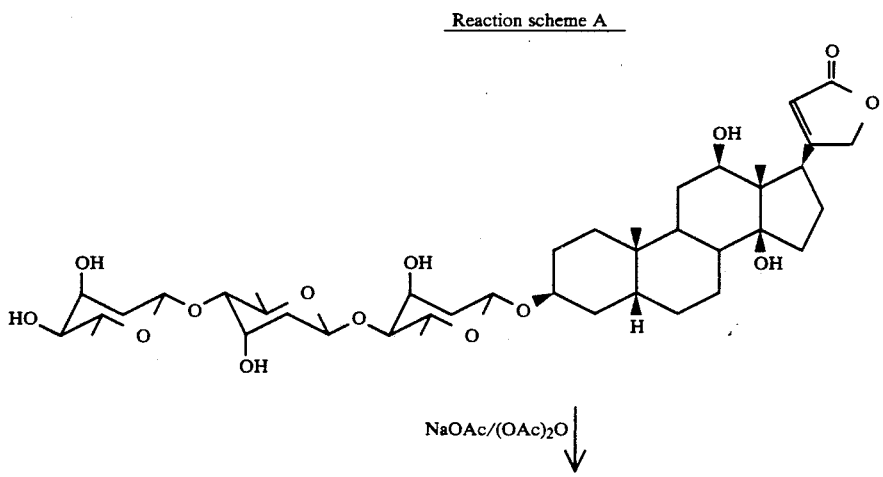

-continued
Reaction scheme A
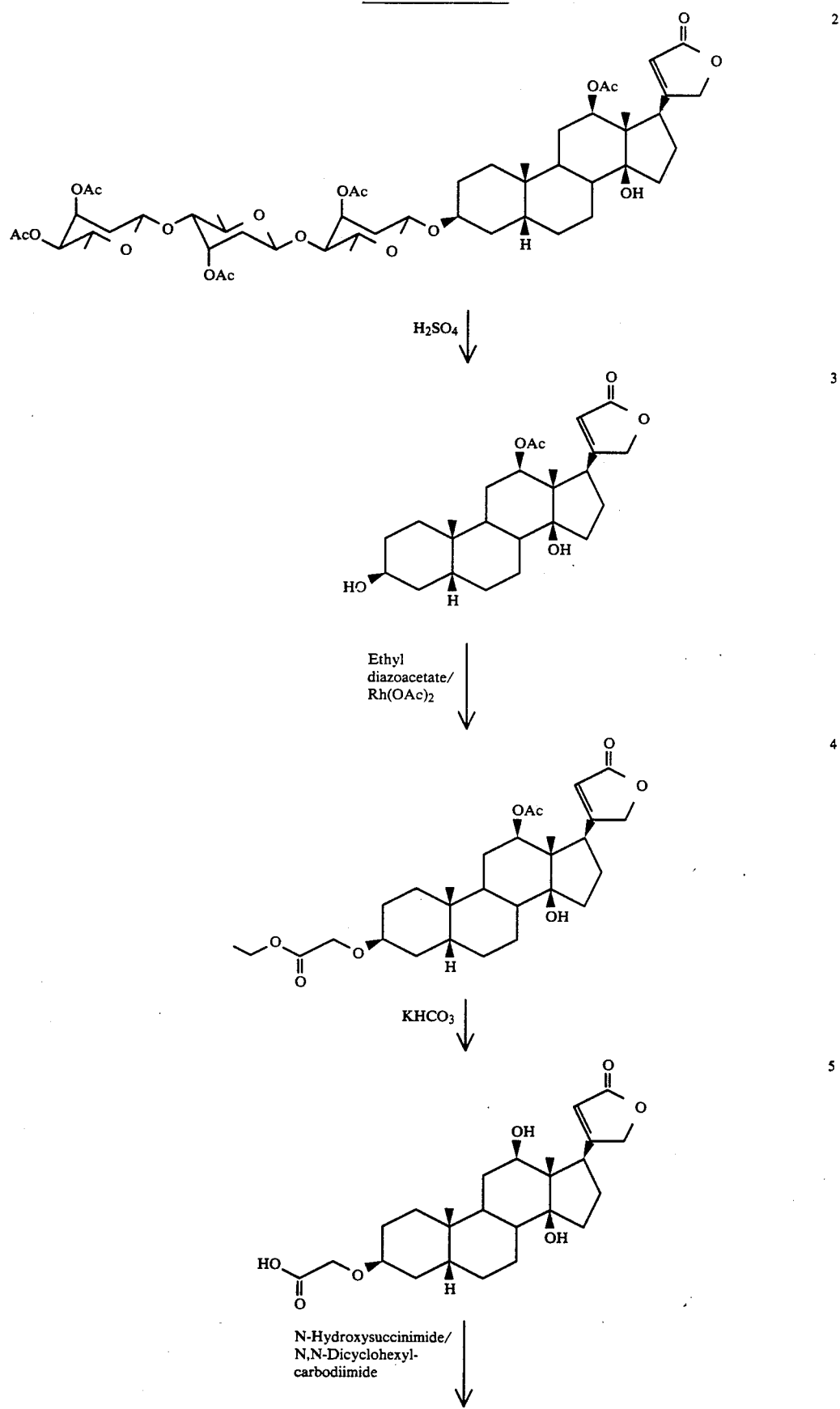

-continued
Reaction scheme A

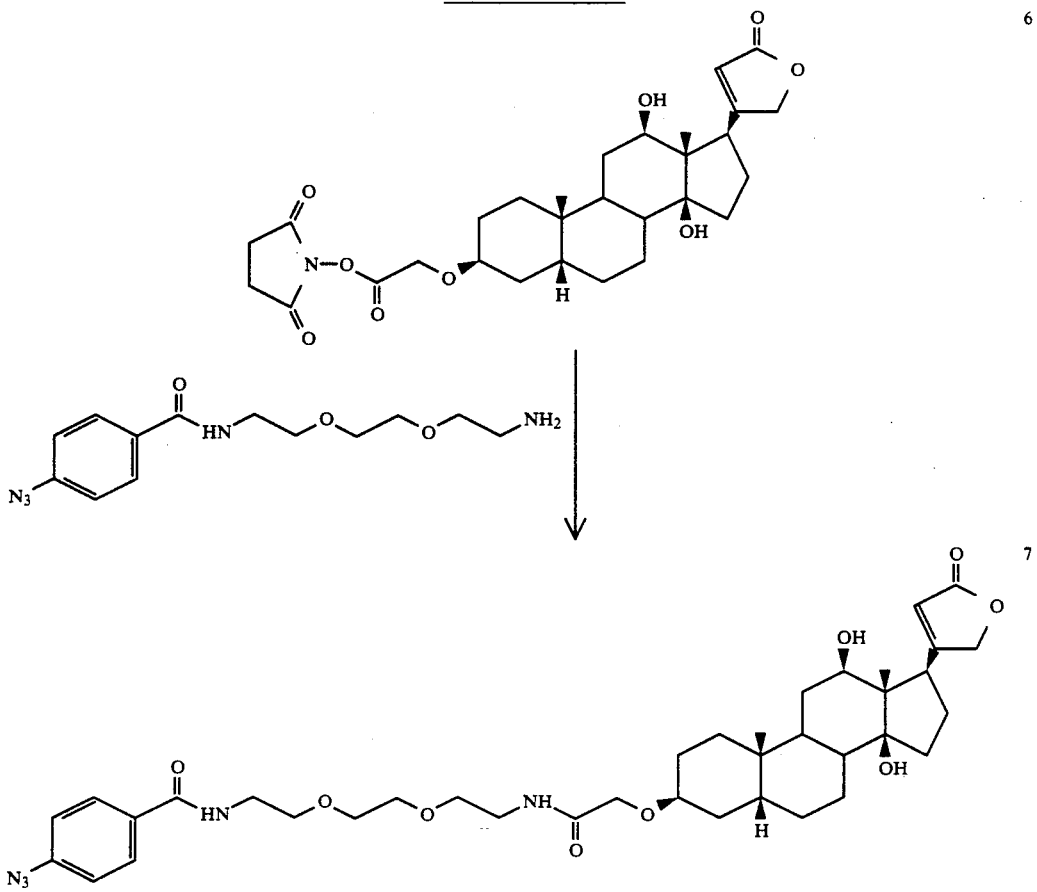

EXAMPLE 1

PREPARATION OF PENTAACETYLDIGOXIN (2)

78 g. (0.1 mole) digoxin are dissolved in 1 liter of acetic anhydride and mixed with 49.2 g. (0.6 mole) anhydrous sodium acetate and the reaction mixture is stirred under reflux for 1 hour. The solution is then evaporated under waterpump vacuum, the residue is dissolved in 1 liter ethyl acetate and filtered off from any insoluble material present. The filtrate is washed three times with, in each case, 0.5 liters of water, dried with 50 g. anhydrous sodium sulphate and evaporated under waterpump vacuum. The crude product obtained still contains some acetic anhydride. Yield 110 g. of a viscous oil. TLC: silica gel; ethyl acetate/chloroform (1:1 v/v);
$R_f = 0.33$.

EXAMPLE 2

Preparation of 12-O-acetyl-digoxigenin (3)

The evaporation residue (compound 2) obtained according to Example 1 is dissolved in 2 liters of methanol, mixed with 2 liters of 0.1N sulphuric acid and stirred under reflux for 1 hour. Thereafter, it is extracted once with 1.8 liters and once with 600 ml chloroform, the combined extracts are washed twice with, in each, 1 liter of water, dried over 50 g. anhydrous sodium sulphate and evaporated under waterpump vacuum. The oil obtained (95 g.) is dissolved, with gentle warming, in 250 ml ethyl acetate and left to stand at ambient temperature. After a short time, crystallization commences. Crystallization is allowed to take place for about 4 hours at ambient temperature and for a further 2 hours at +4° C. The solid material is then filtered off with suction and briefly washed with about 100 ml ethyl acetate. Yield 31 g. of colorless crystals. TLC: silica gel; ethyl acetate; $R_f = 0.50$.

EXAMPLE 3

PREPARATION OF 12-O-ACETYLDIGOXIGENIN 3-CARBOXYMETHYLETHER (CME)-ETHYL ESTER (4)

28.1 g. (65 mMole) of compound (3) obtained according to Example 2 are suspended in 250 ml tetrahydrofuran and, in the course of 5 hours, 69 ml (0.65 mole) ethyl diazoacetate in 50 ml tetrahydrofuran are added dropwise thereto, while stirring. For starting the reaction and, in each case, after 1 hour, there are added thereto 50 mg rhodium (II) acetate. Since a slight heating up of the reaction solution thereby takes place, it is recommended to cool the solution with a water bath (25° C.). Stirring is continued for 16 hours at ambient temperature, then, according to the above-described process, 69 ml ethyl diazoacetate and, in all, 250 g. rhodium acetate are added thereto. After a further 16 hours, the whole procedure is repeated a third time. Subsequently, post-reaction is allowed to take place for 1 day, the reaction mixture is then mixed with 250 ml methanol and the solution is evaporated in a vacuum. The oily residue is digested three times with, in each case, 1 liter of petroleum ether and, after decanting, dissolved in 100 ml chloroform/ethyl acetate (2:1 v/v). The crude product is applied to a silica gel column (8.5×50 cm) and eluted with chloroform/ethyl acetate (2:1 v/v). The fractions containing the pure product (4) are combined and the solvent is removed under waterpump vacuum.

Yield: 18.2 g. of a viscous oil.

TLC: silica gel; ethyl acetate/petroleum ether (2:1 v/v;

$R_f=0.60$.

EXAMPLE 4

Preparation of digoxigenin-3-carboxymethyl ether (cme) (5)

15.5 g. (30 mMole) of the compound (4) obtained according to Example 3 are dissolved in 470 ml methanol and mixed with a solution of 6.05 g. (60 mMole) potassium hydrogen carbonate in 100 ml of water. The reaction mixture is stirred under reflux and the course of the reaction is monitored every half hour by means of thin layer chromatography. When the concentration of the educt only amounts to about 5% (after about 3.5 hours), the reaction is discontinued. The pH is adjusted to 5.0 with glacial acetic acid, the methanol is evaporated off under waterpump vacuum and the residue is diluted with water to about 500 ml. The crude product is extracted twice with, in each case, 200 ml ethyl acetate, washed with water and the organic solution is dried with anhydrous sodium sulphate. After evaporation, the 11 g. of oil thereby obtained are dissolved in 40 ml ethyl acetate/glacial acetic acid (9:1 v/v) and left to stand at ambient temperature. After a short time, crystallization commences. The reaction mixture is cooled to +4° C. for 1 hour, the solid material is filtered off with suction and then washed with about 20 ml ethyl acetate/glacial acetic acid (9:1 v/v). There are obtained 3 g. of product (5) which is dried in a desiccator over potassium hydroxide.

The mother liquor is evaporated and the residue (about 7.5 g.) applied to a silica gel column (8.5×40 cm). After elution with ethyl acetate/glacial acetic acid (9:1 v/v) and evaporation of the appropriate fractions, there are obtained a further 2.2 g. of product (5) which can still contain traces of 12-O-acetyldigoxigenin-3-cme.

Yield: 5.2 g of colorless solid material.

TLC: silica gel, ethyl acetate/glacial acetic acid (9:1 v/v); $R_f=0.42$.

EXAMPLE 5

Preparation of digoxigenin-3-cme-O-succinimide (6)

4.49 g. (10 mMole) of the digoxigenin-carboxylic acid (5) obtained according to Example 4, together with 1.27 g. (11 mMole) N-hydroxysuccinimide, are dissolved in 140 ml anhydrous tetrahydrofuran and mixed with a solution of 2.27 g. (11 mMole) N,N'-dicyclohexylcarbodiimide in 20 ml anhydrous tetrahydrofuran. The reaction mixture is stirred for 20 hours at ambient temperature, then filtered off from the precipitated urea and the solution evaporated under waterpump vacuum. The residue is dissolved in 150 ml ethyl acetate, filtered and washed with 100 ml of water. The organic solution is thereafter immediately dried with 5 g. anhydrous sodium sulphate and evaporated. The crude product is dissolved in about 30 ml ethyl acetate, filtered and poured slowly, while stirring, into 200 ml diisopropyl ether. The precipitated ester (6) is filtered off with suction and dried in a desiccator over phosphorus pentoxide.

Yield: 5.1 g. of colorless powder.

TLC: silica gel RP-18; nitromethane/ethanol (9:1 v/v);

$R_f=0.66$.

EXMAPLE 6

Preparation of photo-digoxigenin (7)

272 mg (0.5 mMole) of the active ester (6) obtained according to Example 5 are dissolved in 10 ml dioxan and mixed with a solution of 161 mg (0.55 mMole) N-(4-azidobenzoyl)-1,8-diamino-3,6-dioxaoctane in 5 ml of water. Stirring is allowed to continue for 2 hours at ambient temperature, the dioxan is then evaporated under waterpump vacuum and the residue is diluted with 50 ml of water. The aqueous phase is extracted twice with, in each case, 50 ml ethyl acetate, the combined organic extracts are dried with 5 g. anhydrous sodium sulphate and evaporated. The residue is digested with 100 ml of diisopropyl ether, filtered off with suction and dried in a desiccator over anhydrous calcium chloride. Yield: 216 g. of colorless power.

TLC: silica gel RP-18, nitromethane/ethanol (9:1 v/v);

$R_f=0.36$.

The following reaction scheme B shows schematically the stepwise preparation of Dig-11-dUTP which can be used, for example, as hapten label for detection of nucleic acids by hybridization with a complementary labelled nucleic acid, for example according to the following Examples 7 to 9;

Reaction scheme B
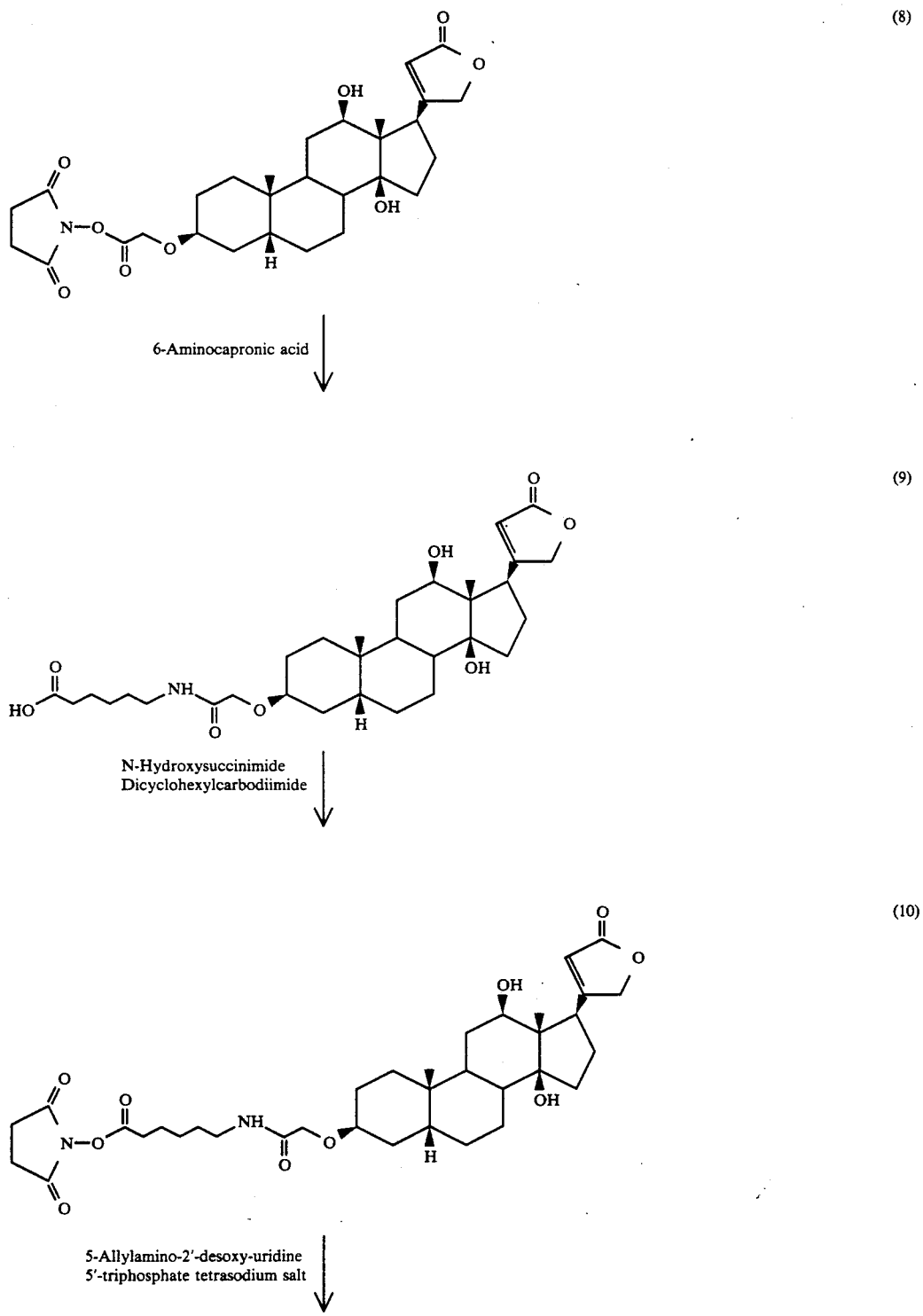

-continued
Reaction scheme B

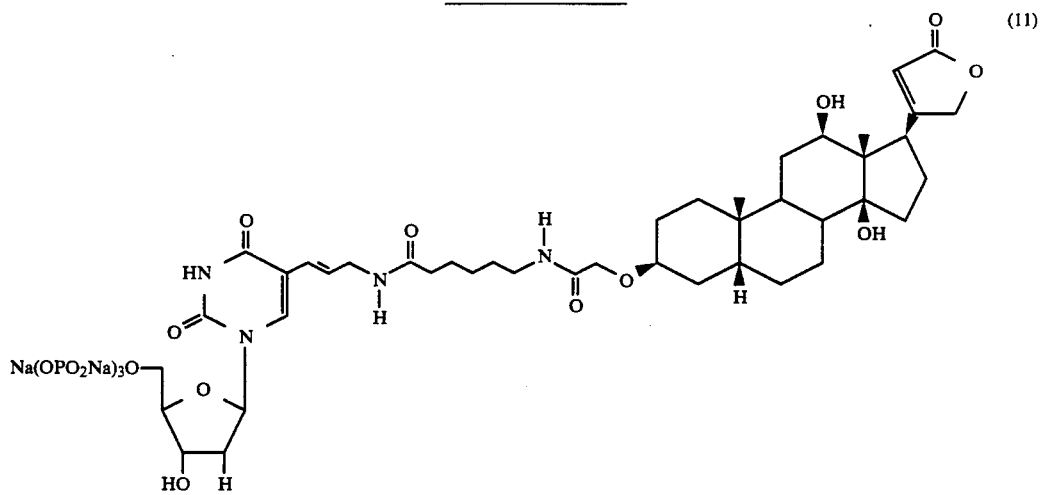

EXAMPLE 7

Digoxigenin-3-carboxymethyl ether ε-amidocapronic acid (9)

$C_{31}H_{47}NO_8$ M.W. 561.3

In a 250 ml round-bottomed flask, 465 mg digoxigenin-3-carobxymethyl ether N-hydroxysuccinimide ester (8) (0.85 mMol) are dissolved in 15 ml dimethylformamide and a suspension of 112 mg 6-aminocarpronic acid (0.85 mMole) and 0.12 ml triethylamine in 2 ml dimethylformamide added thereto. The mixture is magnetically stirred overnight at ambient temperature, a homogeneous solution thereby gradually being formed. After this time, according to thin layer chromatography (silica gel: ethyl acetate/petroleum ether/ethanol (1:1:1 v/v/v), detection: spraying with a mixture of 10 ml glacial acetic acid+0.2 ml concentrated sulphuric acid+0.1 ml anisaldehyde and heating to 120° C. until the appearance of blue-black spots; $R_f$ about 0.7; $R_f$ digoxigenin-OSu ester about 0.85), the reaction is practically complete.

The dimethylformamide is completely distilled off in a high vacuum and the remaining oil is dissolved in 5 ml of water with the addition of a concentrated aqueous solution of ammonia. The "free" digoxigenin amidocapronic acid is then separated out by the addition of 22.5 ml aqueous citric acid solution (100 g. citric acid/liter). The resinous-viscous mass becomes solid upon trituration with water. It is filtered off with suction, washed several times with water and finally dried over phosphorus pentoxide under oil pump vacuum.

Yield: 325 mg (68% of theory).

EXMAPLE 8

Digoxigenin-3-carboxymethyl ether ε-amidocapronic acid N-hydroxysuccinimide ester (10)

$C_{35}H_{50}N_2O_{10}$ M.W. 658.8

In a 100 ml round-bottom flask, 320 mg digoxigenin-3-carboxymethyl ether ε-amidocapronic acid (9) (0.57 mMole) are dissolved in a 2 ml anhydrous dimethylformamide and successively mixed with 70 mg N-hydroxysucciniide (0.6 mMole), as well as 130 mg dicyclohexylcarbodiimide (0.63 mMole). The reaction mixture is stirred overnight at ambient temperature, filtered off with suction the next day from precipitated dicyclohexylurea and the dimethylformamide is stripped off under oil pump vacuum. The oil remaining behind is taken up in 2 ml ethyl acetate and introduced in about 15 ml ice-cold (−20° C.) petroleum ether. The precipitated initially stilled resinous-viscous product is triturated several times with ice-cold dry petroleum ether until it becomes solid. After drying over phosphorus pentoxide in a vacuum, there are obtained 315 mg of product; 84% of theory.

Elementary analysis:
calc.: C 63.8% H 7.6%; N 4.2%
found: C 63.2%; H 7.6%; N 4.0%.

EXAMPLE 9

Digoxigenin-3-carboxymethyl ether ε-amidocaproyl-[5-(amidoallyl)-2'-desoxyuridine-5'-triphosphate]-tetrasodium salt (11) (Dig-11-dUTP)

$C_{43}H_{61}H_4Ha_4O_{21}P_3$ M.W. 1154.7

245 mg (0.37 mMole) Digoxigenin-3-carboxyethyl ether ε-amidocapronic acid N-hydroxysuccinimide ester (10) are dissolved in 7 ml diemthylformamide and added to a solution of 20 mg (0.37 mMole) 5-allylamino-2'-desoxyuridine-5'-triphosphate tetralithium salt in 6 ml of water. 6.2 ml. 0.1 mole/liter sodium borate buffer (ph 8.5) are added to the mixture and then stirred overnight at ambient temperature (about 15 hours). In a paper electrophoresis (0.05 mole/liter citrate buffer, pH 5.0) one observes in ultra-violet light after this time, besides some unreacted allylamino-dUTP, a somewhat lower running fleck of the desired compound (alternative: thin layer chromatography on silica gel, elution agent isobutyric acid/concentrated aqueous solution of ammonia/water 66:1:33, detection in ultra-violet light or spraying with anisaldehyde reagent—see Example 7; $R_f$ value: 5-allylamino-dUTP 0.2; Dig-amidocapronic acid OSu ester 0.6; Dig-11-dUTP 0.45).

For purification, the reaction mixture is evaporated at oil pump vacuum to a solid residue which is taken up in 200 ml water and applied to an ion exchanger column (DEAE-Sephadex A25, $HCO_3^-$ form, column dimensions 1.5×30 cm). After application to the column, this is briefly washed with water and then eluted with a gradient of, in each case, 1 liter of water to 0.4 mole/liter triethylammonium bicarbonate (pH 8). The fractions containing the pure product are combined, concentrated in a vacuum and freed from excess triethylammonium bicarbonate by repeated evaporation with methanol (no longer an odour of free triethylamine). The contents of the flask used for the reaction are taken up in a little water, the solution is passed over a short cation exchanger column of Dowex 50 WS8 (1×10 cm) in the Na+ form, the column is washed with water until the water is free of ODE (measurement in ultraviolet light at 240 nm) and then evaporated in a vacuum to about 20 ml. After lyophilization, there are obtained 195 mg (45% of theory) of Dig-11-dUTP-Na4 in the form of a white powder.

Analysis: water determination 7.9%

Elementary analysis: (taking into account the water content):

calc.: C 41.2% H 5.3%; N 4.4%; P 7.4%
found: C 41.0%; H 5.4%; N 4.6%; P 7.2%

Ultra-violet spectrum (phosphate buffer pH 7.0): maxima: 220 nm, 290 nm.

Dig-11-dUTP can be introduced into a nucleic acid according to the "random primed" DNA labelling method (DNA labelling and Detection Kit Non-radioactive, Order No. 1093657, Boehringer Mannheim GmbH; see Feinberg, A. P. and Vogelstein, B., Anal. Biochem., 132, June /1983), a nucleic acid probe thereby being obtained for the detection of nucleic acids complementary thereto, which probe contains digoxigenin as labelling hapten.

It will be understood that the specification and examples are illustrative but not limitative of the present invention and that other embodiments within the spirit and scope of the invention will suggest themselves to those skilled in the art.

We claim:

1. Digoxigenin derivative of formula:

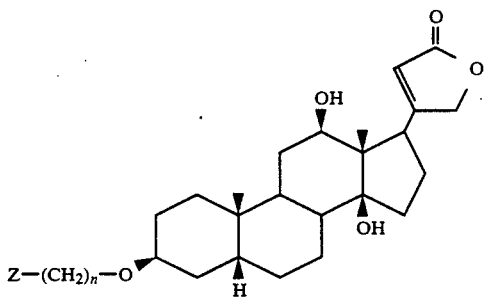

wherein n is a whole number from 1 to 4, and Z is —CN, —COOC$_2$H$_5$,

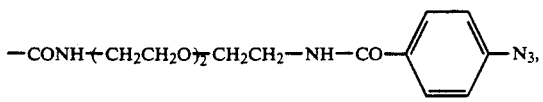

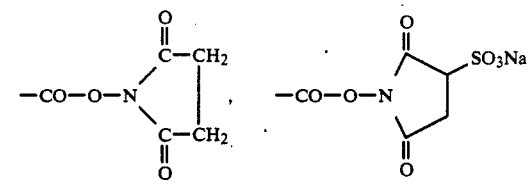

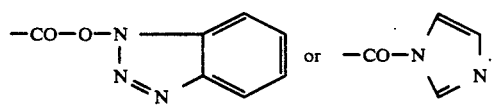

2. Digoxigenin derivative of claim 1, wherein n is 1.

3. Digoxigenin conjugate of the formula:

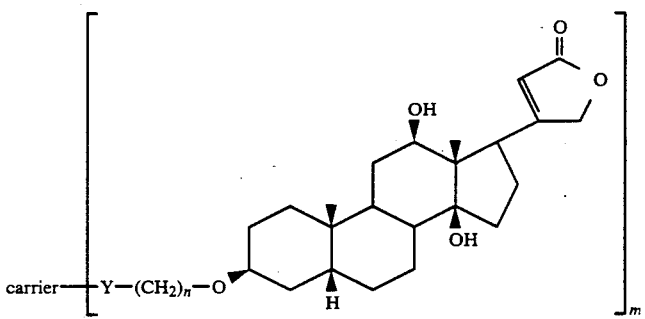

wherein said carrier is an immunogenic protein or polypeptide, a nucleic acid or a labelled immunocomponent of a labelled digoxigenin immunoconjugate, m is a whole number from 1 to the number of coupling positions available on said carrier, and Y is

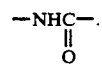

4. Digoxigenin conjugate of claim 3, wherein said carrier is an immunogenic protein or polypeptide.

5. Digoxigenin conjugate of claim 3, wherein said carrier is a nucleic acid.

6. Digoxigenin conjugate of claim 3, wherein said carrier is a labelled immunocomponent.

* * * * *